United States Patent [19]

Segar et al.

[11] 4,212,079
[45] Jul. 8, 1980

[54] ELECTRONIC CALORIE COUNTER

[75] Inventors: Richard B. Segar, Largo, Md.; Lewis C. Marascalco, Pittsburgh, Pa.

[73] Assignee: GPD, Inc., Mitchellville, Md.

[21] Appl. No.: 907,338

[22] Filed: May 18, 1978

[51] Int. Cl.$^2$ ............................................. G06M 3/08
[52] U.S. Cl. ........................... 364/900; 235/92 DP; 235/92 CP; 364/415
[58] Field of Search ............... 73/190 R; 235/92 MT, 235/92 NT, 92 DP, 92 SA, 92 CP, 92 MS; 364/413, 550, 715, 200 MS File, 900 MS File, 415

[56] References Cited

U.S. PATENT DOCUMENTS

| | | | |
|---|---|---|---|
| 3,984,666 | 10/1976 | Barron | 235/92 MT X |
| 4,100,401 | 7/1978 | Tutt et al. | 364/413 X |
| 4,101,071 | 7/1978 | Brejnik et al. | 235/92 MT |

OTHER PUBLICATIONS

Moran, Karen M., "Electronic Diet Controller," *Computer Design*, Aug. 1977, pp. 116-118.

*Primary Examiner*—Raulfe B. Zache
*Attorney, Agent, or Firm*—Armstrong, Nikaido, Marmelstein & Kubovcik

[57] ABSTRACT

A calorie monitoring device is provided for providing a visual output which compares the number of calories burned by an individual versus the calorie intake for the individual. The device has a keyboard which functions as a first input to input the calorie intake of the individual. The calorie intake input is applied to a first calculator through an interface and the calculator adds the calorie intake input to the total calorie intake in storage and displays the new total calorie intake. The keyboard also functions as a second input to receive a value indicative of the calories burned per unit of time for the individual under normal conditions. This value is applied to a second calculator through the interface circuit. The second calculator calculates and displays the total number of calories burned during a total time period which extends over a plurality of the predetermined time periods. Thus, the second calculator provides an output which is a real time display of the total calories burned by the individual.

The device also includes an exercise mode circuit which controls the second calculator to add, to the total calories burned, additional calories when the individual exercises. The exercise mode circuit can be adjusted to add calories burned which are indicative of the level of exercise being performed.

10 Claims, 5 Drawing Figures

| | |
|---|---|
| +,−,X,÷ | ——— BASIC ARITHMETIC OPERATORS |
| • | ——— DECIMAL POINT |
| 0,1,2,3,4,5,6,7,8,9 | ——— INTERGERS |
| C, CE | ——— CLEAR, CLEAR ENTRY |
| M+ | ——— ADD DISPLAY TO MEMORY |
| X→M | ——— REPLACE MEMORY WITH DISPLAY |
| RM | ——— RECALL MEMORY |
| ↕ | ——— PLACE DISPLAY CONTENTS (X REG) INTO Y REGISTER FOR TEMPORY STORAGE |
| ↔ | ——— USED AS MEANS TO INTERUPT ONE IC WHILE DATA IS INPUT INTO THE OTHER |

CALCULATOR INPUT DEFINITIONS

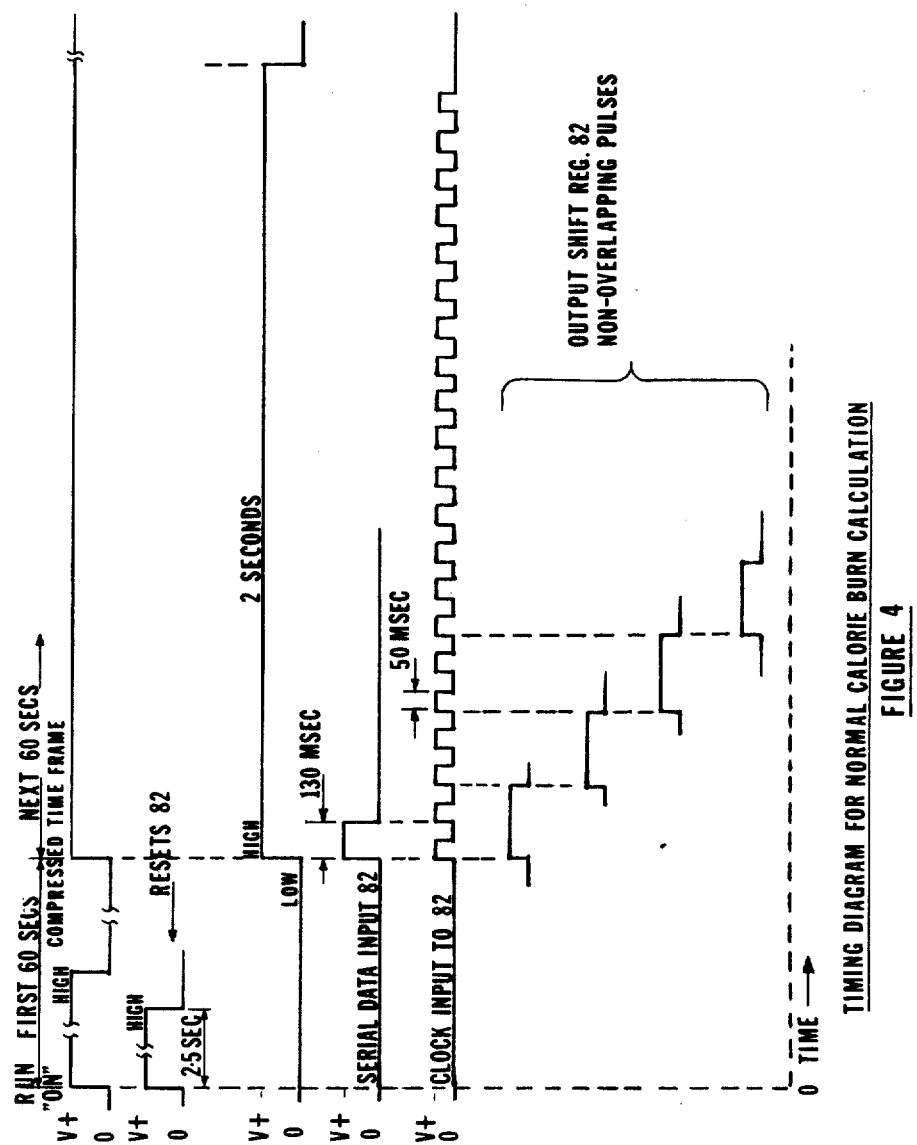

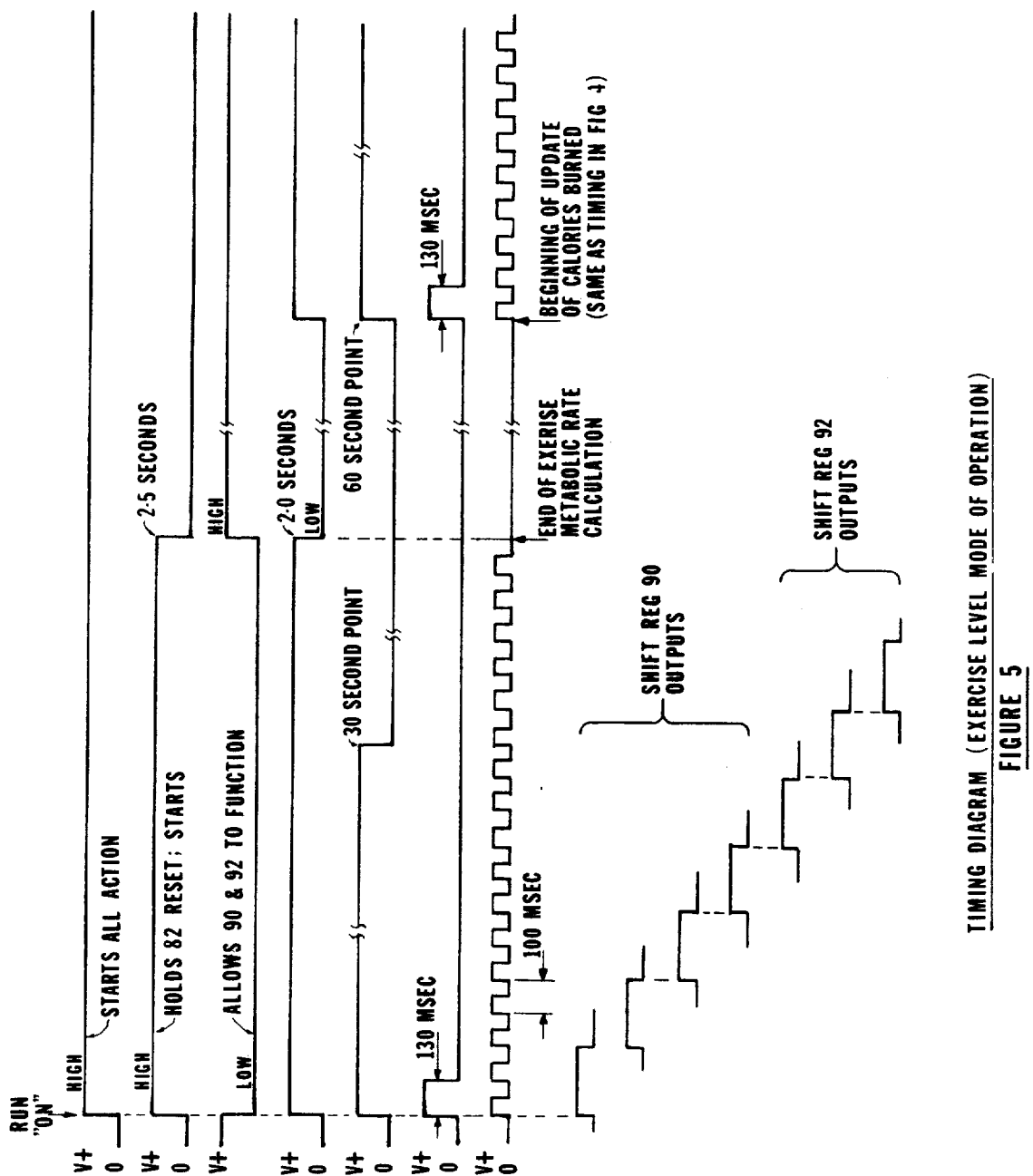

ELECTRONIC CALORIE COUNTER

BACKGROUND OF THE INVENTION

1. Field of the Invention

The present invention is directed to a calorie monitoring device and, more particularly, to a calorie monitoring device which calculates and displays the calorie intake of an individual and calculates and displays on a real time basis the number of calories burned by the individual.

2. Description of the Prior Art

In order to effectively control one's weight, it is necessary to provide a proper balance between the caloric input and the number of calories burned. For example, if an individual desires to lose weight, then it is necessary that the number of calories consumed, or the calorie intake, be less than the number of calories which are burned as a result of the normal activity and exercise by the individual. If the individual wishes to merely maintain his weight, then it is necessary that the number of calories consumed be approximately equal to the number of calories burned.

Heretofore, there have been no devices available which provide, first, for a real time display of the number of calories consumed and, second, a real time display for the number of calories burned in a manner which provides for a quick visual comparison, thus enabling an individual to control the balance of these two factors.

Although it would have been possible for an individual to keep track of the number of calories consumed by adding the number of calories consumed with a pocket calculator, there is still no way of automatically calculating the number of calories burned on a real time basis.

SUMMARY OF THE INVENTION

It is the primary object of the present invention to provide a calorie monitoring device which provides a display of the number of calories consumed by an individual and the number of calories burned by an individual, thereby enabling the individual to compare these two values on a real time basis.

It is another object of the present invention to provide a calorie monitoring device which calculates and displays the number of calories burned by an individual performing his normal activities and adjusts the number during each sequential short time period to thereby provide a real time value of the number of calories burned.

It is still another object of the present invention to provide an exercise mode circuit which enables the number of calories burned to be adjusted to accurately reflect the number of calories burned when the individual is performing exercise beyond his normal activities.

It is still another object of the present invention to provide an exercise mode circuit which can be varied in accordance with the intensity or level of the exercise being performed by the individual.

The present invention thus provides a calorie monitoring device which comprises a first input means for receiving an input indicative of calorie intake, or calories consumed, an interface means, and a first calculator means coupled to the first input means by the interface means. The first calculator means comprises a first display for displaying the caloric intake, first storage means for storing the value of caloric intake and first adder means for adding the input of the input means to the value in the first storage means wherein the sum replaces the value in the storage means and is displayed on the display means. A second input means is provided for receiving an input indicative of calories burned per unit of time and a timing circuit is coupled between the second input means and the interface means. A second calculator means is coupled to the second input means and the timing circuit means by the interface means. The second calculator means comprises a second display means for displaying the value of calories burned, a second storage means for storing the input to the second input means and the total value of calories burned, and adder means for adding the value of the input of the second input means to the total value of the calories burned at predetermined time intervals as determined by the timing circuit means, wherein the sum replaces the total value of the calories burned in the storage means and is displayed on the display means.

An exercise mode circuit is provided which is coupled to the second calculator means for operating the second calculator means to add to the value of the calories burned a number of calories dependent upon an amount of exercise performed by the individual.

BRIEF DESCRIPTION OF THE DRAWINGS

FIG. 4 is a timing diagram of the operation of the present invention in the MTR mode;

FIG. 5 is a timing diagram of the operation of the present invention in the exercise mode.

DETAILED DESCRIPTION OF THE PREFERRED EMBODIMENT

Figures 1, 3:
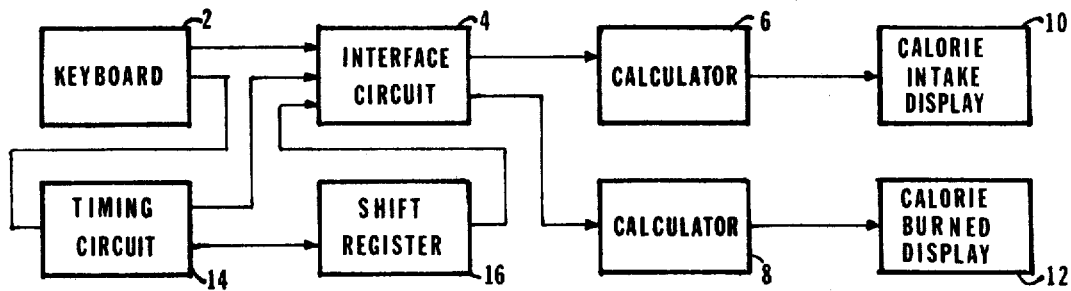
FIG. 1 is a block diagram of the calorie monitoring device of the present invention.
FIG. 3 is a table of calculator input definitions of the calculators used in the preferred embodiment of the present invention.

Referring to FIG. 1, keyboard 2 includes ten keys representing the integers 0-9, mathematical function keys and several mode switches for placing the device in any of several operating modes. The output of the keyboard 2 is connected to interface circuit 4 which interfaces the keyboard 2 with calculators 6 and 8. The value or number calculated in calculator 6 is displayed on calorie intake display 10. The number or value calculated in calculator 8 is displayed on calorie burned display 12. Keyboard 2 also controls timing circuits 14 which in turn control shift registers 16 which generate a plurality of sequential pulses. The output of the timing circuits 14 and shift registers 16 are applied through the interface circuit 4 to the calculators 6 and 8. A table of the inputs to the calculators 6 and 8 is shown in FIG. 3.

Figure 2:
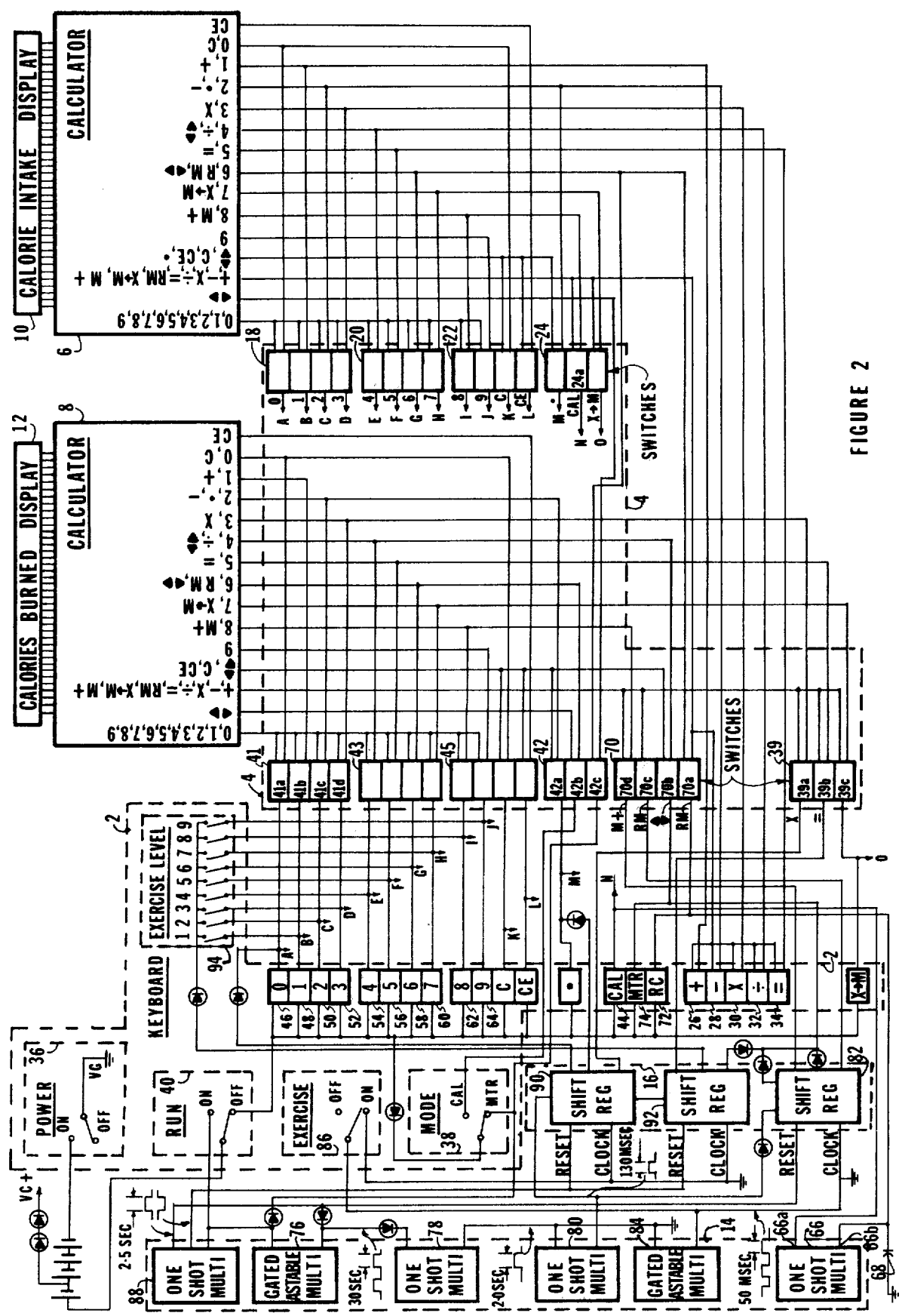
FIG. 2 is a schematic circuit diagram of the preferred embodiment of the present invention.

The calorie intake mode of operation is used to permit an individual to calculate the number of calories which he has consumed through the intake of food. Referring to FIG. 2, calculator 6 and display 10 are used for the calorie intake mode of operation. Calculator 6 is addressed through the switches 18, 20, 22 and 24 of the interface circuit 4 and also directly from switches 26, 28, 30, 32 and 34 of keyboard 2. The calculator 6 is enabled when the main power switch 36 is switched on and also when the mode switch 38 is placed in the CAL (calorie intake) position. Furthermore, the run switch 40 must be placed in the OFF position. When the run switch 40 is in the ON position, the keyboard is disabled for reasons which will be discussed below.

When the mode switch is in the CAL position, it removes a plus voltage from input 42a of switch 42 and applies a voltage to input 42b thereof. This addresses the ⊶⊷ input to calculator 8 which disables the calculator from accepting further inputs. Concurrently, the ⊶⊷ is removed from calculator 6, thus enabling calculator 6 to accept inputs. If the mode switch is placed in the MTR (metabolic rate) position, then calculator 6 is disabled to prevent it from receiving further inputs and calculator 8 is enabled so that it receives further inputs.

Once calculator 6 has been enabled to receive inputs by the placing of the mode switch 38 in the CAL position, a number corresponding to the amount of calories consumed by the individual is entered into the device via the keyboard. The number will appear on display 10. A CAL key 44, which is part of keyboard 2, is then momentarily depressed and the number which has just been entered into the keyboard and displayed on display 10 is added to the total calorie intake stored in the memory of calculator 6, and the new total is stored in the memory of calculator 6 and displayed on calorie intake display 10.

As additional calories are consumed by the individual, they are entered into the device in the same manner, and thus the number appearing on display 10 is the total number of calories which have been consumed during a given time period.

Referring to the operation in greater detail, the number of calories consumed, or the calorie intake, is entered by depressing the integer keys 46-64 on the keyboard. When the CAL key 44 is momentarily depressed, a positive pulse is applied to input 24a of switch 24 and to input 66a of one shot multivibrator 66. The pulse at input 24a addresses the M+ (add to memory) function of calculator 6, such that the number previously entered is added to the memory. The pulse at input 66a causes output 66b to go high, which charges capacitor 68, which is connected to input 70a of switch 70. The capacitor 68 continues to charge until it reaches the threshold voltage of switch 70, which then operates switch 70. The delay is necessary in order to provide the proper sequencing of inputs to the calculator 6. When the threshold voltage of switch 70 is reached, output 70a address the RM (recall memory) function of calculator 6, which recalls the total in the memory and displays it on display 10.

The calculator 6 and display 10 can be used as a normal four-function calculator with the mode switch 38 in the CAL position. After using the unit as a calculator, the calorie intake total can be recalled from the calculator memory by depressing key 72 on the keyboard.

The calories burned display 12 displays the total number of calories burned by the individual on a real time basis. In other words, the display is updated on a periodic basis, such as once every minute, to add to the total displayed, the number of calories burned during each incremental time period. The calories burned operation of the device is based on the fact that the human body consumes energy, that is, burns calories at a specific rate based on numerous factors. If the applicable burn rate is established and totalized per unit of time (that is, for example, calories per minute times minutes), then the total number of calories burned results. The calorie monitoring device of the present invention does this by entering into the device via the keyboard a metabolic rate for the individual using the device. This metabolic rate is then added to a running total on a per minute time basis with the total being accumulated in the calculator memory and recalled for display.

In order to place the device in a mode for calculating calories burned, mode switch 38 is switched to the MTR mode. The metabolic rate of the individual, which has been calculated previously using a mathematical formula, is then entered in the keyboard using number keys 46-64. After the number is entered on the keyboard, MTR key 74 is operated and the metabolic rate is stored in a temporary storage register in calculator 8.

In addition to the circuit shown in FIG. 2, reference is now made to FIG. 4, which is a timing diagram for the operation of the device when in the MTR mode.

Once the metabolic rate has been entered into the device, run switch 40 is placed in the ON position which activates gated astable multivibrator 76. The multivibrator 76 has a period of 60 seconds. At the end of the first 60 seconds, the output of multivibrator 76 goes high, applying a voltage to the input of one shot multivibrator 78, which has an output pulse of approximately 2 seconds. The output of one shot multivibrator 78 is applied to the input of one shot multivibrator 80, which produces an output pulse of 130 milliseconds. The output of one shot multivibrator 80 is applied to the serial data input of shift register 82. Concurrently, the 2 second pulse from one shot multivibrator 78 is applied to gated astable multivibrator 84, the output of which is a series of pulses having a pulse width of 50 milliseconds. The 50 millisecond pulse train is used to clock shift register 82 and is thus applied to the clock input thereof. The output of the shift register 82 is four non-overlapping sequential pulses, each with a duration of 200 milliseconds. These sequential pulses are connected to switch 70 which operates calculator 8. The first pulse is applied to calculator 8 through switch 70b; this first pulse causing the metabolic rate value which has been stored in a temporary register (Y) in calculator 8 to be placed into a display register (X) in calculator 8. The second pulse is applied to the calculator through switch 70d, which causes the number in the display register to be added to the value stored in the calculator memory. The third pulse is applied to the calculator through switch 70b, which takes the number in the X register and returns it to the Y register for use at the end of the next 60 second timing cycle. The fourth pulse is applied to the calculator through switch 70a and it recalls the total in the memory and displays its accumulated total, which is the total number of calories burned on the calorie burned display 12.

Thus, the calories burned display displays a number which is the total number of calories burned, and this number is changed every minute by adding to it the number of calories burned per minute.

The calorie monitoring device of the present invention has the capability of allowing the user to place the unit in a mode of operation representing exercise that the individual is performing. The unit updates the calories burned total at a calorie per minute metabolic rate corresponding to the particular exercise in relation to the individual's weight. Because the weight of the individual using the device is different for each individual, the metabolic rate for an exercise level must be calculated by multiplying a base rate of calories per minute per pound times the number of pounds which the individual weights in order to yield a calories per minute result. This calculation is automatically performed by the present invention, and thus enables the device to accurately reflect the number of calories burned on the calories burned display 12.

Referring to FIG. 2 and the timing diagram of FIG. 5, the device is placed in the exercise mode by placing exercise switch 86 in the ON position. Switch 38 is left in the MTR position and run switch 40 is placed in the OFF position. The individual enters his weight in the keyboard using number switches 46-64 and then depresses MTR switch 74 to enter the weight into calculator 8. One of the exercise level switches 94 is then selected which is indicative of the level of exercise being performed. For example, if the exercise is light, such as walking, exercise level switches 1, 2 or 3 might be selected, whereas if the exercise is very vigorous, such as playing basketball or racquetball, a high level such as 7, 8 or 9 should be selected. Once the selected exercise level switch has been switched to the ON position, the run switch 40 is switched to its ON position, which starts the sequence.

When run switch 40 is placed in the ON position, one shot multivibrator 88 is activated which produces an output of two complementary pulses, each having a pulse width of 2.5 seconds. The positive pulse is connected to the reset input of shift register 82, which holds the shift register in the reset mode for 2.5 seconds. Simultaneously, the negative 2.5 second pulse is applied to the reset inputs of shift registers 90 and 92, which allows them to function during the 2.5 second time interval. At the conclusion of the 2.5 second interval, shift register 82 is activated and shift registers 90 and 92 are disabled.

As seen in FIG. 5, shift registers 90 and 92 produce a series of seven non-overlapping sequential pulses which control the calculator 8 so that it calculates the number of calories burned as a result of the exercise being performed by the individual. The control of the calculator 8 is as follows:

The first pulse is applied to calculator 8 through switch 39a which activates the multiply operation. The second pulse is applied through switch 42c to the decimal point input of calculator 8. The third pulse is applied through switch 41a to enter a zero in the calculator. The fourth pulse passes through the selected exercise level switch and through one of the corresponding switch sections of switches 41, 43 and 45 to the numerical input of the calculator corresponding to the selected exercise level. The fifth pulse is applied to the calculator through 39b, which then causes the calculator to perform the multiplication operation using the numbers just previously entered. The seventh pulse is applied to the calculator through switch 70b, which causes the number in the display register, which is the number just previously calculated, to be placed into the temporary storage register replacing the former normal metabolic rate with the newly calculated exercise metabolic rate.

At the end of 60 seconds, astable multivibrator 76 goes high and starts the sequence which operates shift register 82, causing the calculator 8 to recalculate calories burned on a repetitive basis in the manner which has been previously described. However, the number corresponding to the calories burned per minute as a result of the exercise level is now stored in the temporary storage in calculator 8. Thus, the total calories burned is increased each minute by the number of calories burned while performing the exercise rather than by the normal calories burned rate.

When the individual stops exercising, the calories burned per minute under normal activity are then reentered into the calculator in the manner described above, and calories burned display is increased on a repetitive basis by the number of calories burned for normal activity.

In addition to the preferred embodiment described above, other modifications to the device are possible. For example, an alarm or indicator can be included in the device to provide an indication when the calorie intake exceeds the calories burned by a predetermined amount. This would provide an indication to the individual using the device that he must either burn additional calories in order to balance the calories burned with the calories consumed, or he must stop consuming calories and continue to burn calories at his normal rate.

Another modification to the device could be made in the manner of calculating the total calories burned as a result of exercise. In the preferred embodiment, the rate of calories burned is increased to reflect the exercise level. Another technique would be to maintain the same calorie burn rate, but to adjust the time interval at which this rate is added to the total calories burned. In other words if, for example, an individual's metabolic rate is two calories per minute, then during a period of exercise, the total could be changed every half minute, thus adding four calories per minute instead of the normal rate of two.

The calorie monitoring device of the present invention could be packaged in the manner of a normal handheld calculator with two displays thereon, instead of the normal single display. One of the displays will be calorie intake display 10 and the other display would be calories burned display 12. All of the various switches would be on the face of the calculator.

The present invention may be embodied in other specific forms without departing from the spirit or essential characteristics thereof. The presently disclosed embodiments are, therefore, to be considered in all respects as illustrative and not restrictive, the scope of the invention being indicated by the appended claims rather than the foregoing description, and all changes which come within the meaning and range of quivalency of the claims are, therefore, to be embraced therein.

What is claimed:

1. A calorie monitoring device comprising:
   (a) first input means for receiving an input indicative of calorie intake said first input means including a keyboard;
   (b) interface means;
   (c) first calculator means coupled to said first input means by said interface means, said first calculator means comprising:
      (i) first display means for displaying the calorie intake;
      (ii) first storage means for storing the value of calorie intake;
      (iii) first adder means for adding the input of said input means to the value in said first storage means, wherein the sum replaces the value in said storage means and is displayed on said display means;
   (d) second input means for receiving an input indicative of calories burned per unit of time said second input means including said keyboard;
   (e) timing circuit means coupled between said second input means and said interface means;

(f) second calculator means coupled to said second input means and said timing circuit means by said interface means, said second calculator means comprising:
  (i) second display means for displaying the value of calories burned;
  (ii) second storage means for storing the input to said second input means and the total value of calories burned; and
  (iii) adder means for adding the value of the input of said second input means to the total value of the calories burned at predetermined intervals as determined by said timing circuit means, wherein the sum replaces the total value of the calories burned in said storage means and is displayed on said display means; and
(g) a mode switch means coupled between said keyboard and said interface means for operably coupling said keyboard to one of said first or second calculator means through said interface means and for disabling the other of said first or second calculator means through said interface means.

2. A calorie monitoring device as set forth in claim 1 including a run switch means coupled between said keyboard and said timing circuit means and having a first state for disabling said keyboard and a second state for enabling said keyboard.

3. A calorie monitoring device as set forth in claim 2 wherein said timing circuit means comprises a pulse generating means for generating a predetermined number of pulses during the period of said timing circuit means.

4. A calorie monitoring device as set forth in claim 3 wherein said interface means comprises a plurality of switch means connected to said pulse generating means and to said second calculator means wherein, when said pulses are sequentially applied to said switch means, said switch means change state and thereby control the operation of said second calculator means.

5. A calorie monitoring device as set forth in claim 5 wherein said pulse generating means comprises:
  (a) a first gated astable multivibrator;
  (b) a first one shot multivibrator having an input coupled to the output of said first gated astable multivibrator;
  (c) a second one shot multivibrator having an input connected to the output of said first one shot multivibrator;
  (d) a first shift register having a gate input connected to the output of said second one shot multivibrator; and
  (e) a gated astable multivibrator having an input connected to the output of said first one shot multivibrator and having an output connected to the clock input of said first shift register wherein the output of said first shift register is said predetermined number of pulses.

6. A calorie monitoring device as set forth in claim 1 or 5 including an exercise mode circuit means coupled through said interface means to said second calculator means for operating said calculator means to add to the value of the calories burned a number of calories dependent upon an amount of exercise performed.

7. A calorie monitoring device as set forth in claim 6 wherein said exercise mode circuit means includes control means for controlling the number of calories added as a function of the intensity of the exercise performed.

8. A calorie monitoring device as set forth in claim 7 wherein said control means controls the number of calories added durng said predetermined time intervals.

9. A calorie monitoring device as set forth in claim 7 wherein said control means controls a time interval at which incremental values are added to the value of the number of calories burned.

10. A calorie monitoring device as set forth in claim 6 wherein said exercise mode circuit means comprises:
  (a) a second shift register having a gate input connected to the output of said second one shot multivibrator;
  (b) a third shift register having a gate input connected to an output of said second shift register; and
  (c) a third one shot multivibrator coupled to said first, second and third shift registers for enabling said first and second shift registers and disabling said third shift register when said exercise mode circuit means is operative, wherein said second and third shift register means produce a series of pulses for controlling the operation of said second calculator means.

* * * * *